United States Patent [19]

Heinsohn et al.

[11] Patent Number: 5,151,358
[45] Date of Patent: Sep. 29, 1992

[54] PROCESSES FOR THE RECOVERY OF NATURALLY PRODUCED CHYMOSIN

[75] Inventors: Henry G. Heinsohn, Pacifica; Jeffrey D. Lorch; Kirk J. Hayenga, both of San Mateo; Raymond E. Arnold, San Francisco, all of Calif.

[73] Assignee: GEnencor International, Inc., South San Francisco, Calif.

[21] Appl. No.: 537,461

[22] Filed: Jun. 13, 1990

Related U.S. Application Data

[63] Continuation-in-part of Ser. No. 365,937, Jun. 13, 1989.

[51] Int. Cl.⁵ .............................................. C12N 9/64
[52] U.S. Cl. ................................. 435/226; 435/815; 435/816; 426/36; 426/42
[58] Field of Search ............... 435/226, 815, 816; 426/36, 42

[56] References Cited

U.S. PATENT DOCUMENTS

| | | | |
|---|---|---|---|
| 2,339,931 | 1/1944 | Keil | 195/68 |
| 3,281,332 | 10/1966 | Munns et al. | 195/66 |
| 3,357,894 | 12/1967 | Uriel et al. | 195/66 |
| 3,415,804 | 12/1968 | Polson | 260/112 |
| 3,816,260 | 6/1974 | Sugiyama | 195/62 |
| 3,834,990 | 9/1974 | Werle et al. | 195/68 |
| 3,890,198 | 6/1975 | Kobayashi et al. | 195/66 R |
| 3,917,510 | 11/1975 | Kitamura et al. | 195/2 |
| 4,016,039 | 4/1977 | Schreiber | 195/66 R |
| 4,144,130 | 3/1979 | Kula et al. | 195/66 R |
| 4,250,084 | 2/1981 | Trainin | 260/112 |
| 4,299,858 | 11/1981 | Aubert et al. | 426/656 |
| 4,305,871 | 12/1981 | Shanbrom | 260/112 B |
| 4,343,735 | 8/1982 | Menge et al. | 260/112 R |
| 4,439,358 | 3/1984 | Coan et al. | 260/112 B |
| 4,461,833 | 7/1984 | Gordon | 435/183 |
| 4,470,969 | 9/1984 | Pancham et al. | 424/101 |
| 4,508,825 | 4/1985 | Kim et al. | 435/201 |
| 4,530,903 | 7/1985 | Leuchtenberger et al. | 435/130 |
| 4,590,161 | 5/1986 | Kula et al. | 435/104 |
| 4,591,563 | 5/1986 | Paul et al. | 435/193 |
| 4,601,986 | 7/1986 | Wegner et al. | 435/255 |
| 4,666,843 | 5/1987 | Subramanian | 435/226 |
| 4,666,847 | 5/1987 | Alford et al. | 435/253 |
| 4,683,294 | 7/1987 | Van Wijnendaele et al. | 530/371 |
| 4,684,723 | 8/1987 | Dove et al. | 530/351 |
| 4,697,003 | 9/1987 | Coan | 530/380 |
| 4,721,673 | 1/1988 | Uren et al. | 435/183 |
| 4,728,613 | 3/1988 | Brewer et al. | 435/222 |
| 4,743,551 | 5/1988 | Subramanian | 435/226 |
| 4,745,063 | 5/1988 | Birschbach | 435/226 |

OTHER PUBLICATIONS

Andersson et al., *Enzyme and Microb. Technol.*, vol. 7, pp. 333–338 (1985).
Marston et al., *Biotechnology.* pp. 800–804 (1984).
Kula et al., "Purification of Enzymes by Liquid-Liquid Extraction" pp. 73–117.
Engstrom and Wong, "Milk Clotting Enzymes and Cheese Chemistry", in *Fundamentals of Dairy Chemistry*, 2d ed., ed. Webb et al., pp. 674–679 (1983).
Foltmann, "General and Molecular Aspects of Rennets" pp. 33–61.

*Primary Examiner*—Charles L. Patterson, J.
*Attorney, Agent, or Firm*—Burns, Doane, Swecker & Mathis

[57] ABSTRACT

Disclosed are methods for the recovery and purification of naturally produced chymosin. In particular, disclosed are methods for the recovery and purification of chymosin from aqueous solutions containing chymosin, pepsin and other contaminants.

28 Claims, No Drawings

PROCESSES FOR THE RECOVERY OF NATURALLY PRODUCED CHYMOSIN

CROSS-REFERENCE TO RELATED APPLICATIONS

This application is a continuation-in-part of U.S. Ser. No. 07/365,937, filed on Jun. 13, 1989, titled "Processes for Recovery and Purification of Chymosin", which is incorporated herein by reference in its entirety.

BACKGROUND OF THE INVENTION

1. Field of the Invention

This invention relates to the recovery and purification of naturally produced chymosin. In particular, this invention is directed to methods for the recovery and purification of chymosin from aqueous solutions containing chymosin which have been obtained from the extraction of natural chymosin sources.

2. State of the Art

Chymosin is a known enzyme which is particularly useful in the preparation of cheese. While natural sources of chymosin include calf stomachs, bovine stomachs, goat stomachs, porcine stomachs, etc., commercial chymosin has heretofore been primarily obtained from the fourth stomach of milk fed calves. This is a result of the fact that such calves produce greater amounts of chymosin as compared to pepsin whereas other chymosin sources generally contain greater amounts of pepsin as compared to chymosin and accordingly, recovery of chymosin from such other sources is more difficult and economically less efficient, i.e., there is less chymosin to recover.

However, due to the recent decrease in calf production, the heretofore preferred natural source of chymosin has declined which, in turn, has provided impetus to developing more efficient methods for the recovery and purification of naturally produced chymosin. Specifically, more efficient methods would result in the improved recovery and purification of chymosin from calf stomachs as well as permit the economical recovery and purification of chymosin from other natural chymosin sources.

A major stumbling block to developing such methodology has been the very high level of contaminants found in the chymosin solution obtained from natural chymosin sources. In addition to pepsin, the aqueous extract obtained from these natural chymosin sources contain other contaminants including, for example, other stomach enzymes and proteins. Such contaminants have complicated the development of efficient recovery and purification methodology.

While numerous methods are disclosed for isolating enzymes from aqueous solutions, such as fermentation beer, none of the references which Applicants are aware of disclose methods for recovering and purifying naturally produced chymosin, especially naturally produced chymosin intermixed with pepsin and other contaminants, which employ a liquid-liquid two phase system.

In this regard, U.S. Pat. No. 4,144,130 describes the use of (1) a mixture of a high molecular weight unsubstituted or substituted polyalcohol, polyether, polyvinylpyrrolidone or polysaccharide and an inorganic salt, (2) a mixture of at least two of the above high molecular weight polymers to recover intracellular enzymes from an aqueous solution into which they have been released from the cells. When a mixture of polyethylene glycol and an inorganic salt is used, the desired intracellular enzyme goes into the top polyethylene glycol layer while the cell debris and other fermentation products go into the lower salt-containing layer. This reference discloses that the partition coefficients for various enzymes recovered in the glycol layer was about 0.3 when a normal cell mass was treated, which could be increased to about 3 when frozen cells were mixed with water and disintegrated to release their enzymes.

Similarly, U.S. Pat. No. 4,728,613, discloses a process for the recovery of extracellularly produced enzymes, such as protease, amylase and microbial rennet, from whole fermentation beer by using an inorganic salt in combination with a polymer selected from the group consisting of polyethylene glycol, an amine derivative of polyethylene glycol, a carboxylate derivative of polyethylene glycol, polypropylene glycol, an amine derivative of polypropylene glycol, a carboxylate derivative of polypropylene glycol, poly(ethylene glycol) ester, polyethyleneimine, trimethylamino-polyethylene glycol, polyvinyl alcohol, polyvinylpyrrolidone and mixtures thereof. The examples of this reference disclose achieving partition coefficients of up to about 80 for such extracellular enzymes.

Likewise, Kula et al., "Purification of Enzymes by Liquid-Liquid Extraction", describes numerous methods for the purification of enzymes by liquid-liquid extraction. Among numerous methods disclosed, Kula et al. disclose that the addition of a polyethylene glycol-/inorganic salt mixture to an aqueous solution containing the enzyme will form a two phase system wherein the polyethylene glycol phase will contain the enzyme. Kula et al. further disclose at page 111 that the phase forming polymer (polyethylene glycol) can be removed from the enzyme by adsorption of the enzyme onto ion exchangers; washing away of the phase forming polymer; and the subsequent recovery of the enzyme.

On the other hand, U.S. Pat. No. 4,508,825 discloses that extracellular protease and amylase co-produced during the fermentation of a microorganism capable of producing them are separated by the addition of polyethylene glycol and a cationic epihalohydrin/polyamine copolymer or dextran polymer to the fermentation medium and allowing the polymers to phase separate to form a protease rich phase and an amylase rich phase.

Also, U.S. Pat. No. 4,591,563, discloses a process for the simultaneous purification and concentration of the dextran-sucrase enzyme from the culture medium on sucrose. In particular, the disclosed method involves the addition of a polyether such as polyethylene glycol so as to form two phases; the first a heavy dextran-rich phase that contains the concentrated and purified dextran-sucrase enzyme, and the second a lighter polyether-rich phase that contains contaminating enzymatic activities, which is eliminate.

In view of the above, it is apparent that the cited art does not disclose the recovery and purification of naturally produced chymosin from aqueous solutions containing pepsin and other contaminants by employing an aqueous two phase system derived from the addition of polyethylene glycol and inorganic salt coupled with the use of an ion exchange resin. On the other hand, industrial or commercial scale recovery and purification of naturally produced chymosin is greatly facilitated by using such a liquid-liquid two phase system for the recovery of chymosin and by using an ion exchange resin for the purification of chymosin.

Accordingly, it is an object of this invention to provide efficient processes for the recovery and purification of naturally produced chymosin from aqueous mixtures containing chymosin, pepsin and other contaminants produced by the aqueous extraction of natural chymosin sources.

It is a further object of this invention to provide a recovery and purification process for naturally produced chymosin wherein recovery is achieved by using a liquid-liquid two phase system and purification is achieved by using an ion exchange resin.

It is still a further object of this invention to provide a recovery and purification process for naturally produced chymosin wherein recovery is achieved by using a liquid-liquid two phase system which provides for the selective recovery of chymosin and pepsin from other contaminants found in the aqueous solution.

It is a further object of this invention to provide a purification process for naturally occurring chymosin from an aqueous/polythylene glycol solution containing chymosin and pepsin.

These and other objects are achieved by the present invention as evidenced by the attached summary of the invention, detailed description of the invention, examples, and claims.

SUMMARY OF THE INVENTION

In one aspect, this invention is a method for recovering and purifying chymosin from an aqueous solution which contains chymosin obtained from natural sources and which additionally contains pepsin and other contaminants which method comprises:
 a) adding to the aqueous solution an effective amount of polyethylene glycol (PEG) and an inorganic salt so as to form a two phase system;
 b) allowing the aqueous solution-polyethylene glycol-inorganic salt mixture to separate into a chymosin and peps in-rich polyethylene glycol phase and a chymosin and pepsin-poor salt phase;
 c) recovering the chymosin and pepsin-rich polyethylene glycol phase,
 d) contacting the chymosin and pepsin-rich polyethylene glycol phase with an ion exchange resin under conditions wherein the chymosin binds to the resin and the polyethylene glycol and pepsin pass through the resin; and
 e) recovering the chymosin from the resin.

Surprisingly, in the extraction step, most of the chymosin and pepsin are partitioned into the polyethylene glycol phase whereas the contaminants other than pepsin remain in the salt phase. Moreover, when the poyethylene glycol phase is contacted with a suitable ion exchange resin, the chymosin binds to the resin whereas the pepsin passes through. Afterwards, the chymosin, substantially free of pepsin and other contaminants (i.e, the amount of contamination is less than about 10% by weight based on the weight of chymosin), is recovered from the resin. Thus, the method of the present invention is an extremely efficient recovery and purification method for naturally produced chymosin.

In general, the pH of the aqueous solution can be any pH at which the chymosin is stable, i.e., about 6.5 or less. However, in a preferred embodiment, it has been found that the use of lower pHs, i.e., pH 3 or less and preferably from about pH 2 to about 2.5, in the aqueous solution result in higher partition coefficients (higher selectivity) for the separation of chymosin into the polyethylene glycol phase as compared to the use of pHs of from above 3 to about 6.5.

Accordingly, a preferred method aspect of the present invention relates to a method for recovering and purifying chymosin from an aqueous solution which contains chymosin obtained from natural sources and which additionally contains pepsin and other contaminants which method comprises:
 a) adjusting the pH of the aqueous solution to less than about 3 and then adding to the aqueous solution an effective amount of polyethylene glycol (PEG) and an inorganic salt so as to form a two phase system;
 b) allowing the aqueous solution-polyethylene glycol-inorganic salt mixture to separate into a chymosin and pepsin-rich polyethylene glycol phase and a chymosin and pepsin-poor salt phase;
 c) recovering the chymosin and pepsin-rich polyethylene glycol phase,
 d) contacting the chymosin and pepsin-rich polyethylene glycol phase with a cation exchange resin under conditions wherein the chymosin binds to the resin and the polyethylene glycol and pepsin pass through the resin; and
 e) recovering the chymosin from the resin.

DESCRIPTION OF THE INVENTION

The separation of various enzymes from aqueous solutions using polymers such as polyethylene glycol of various molecular weights in combination with other polymers, e.g., dextran, or inorganic salts is known in the art. However, this invention is directed in part to the unexpected discovery that chymosin can be efficiently recovered and purified from aqueous solutions containing naturally produced chymosin, pepsin and other contaminants by adding a sufficient amount of both polyethylene glycol and an inorganic salt to the aqueous solution so as to form a two phase system. Under these circumstances, almost all of the chymosin and pepsin is partitioned into the polyethylene glycol phase. This is evidenced by partition coefficients for chymosin and pepsin in the polyethylene glycol phase of greater than about 30 and preferably greater than about 85. On the other hand, most of the other contaminants remain in the salt phase. Thus, this extraction step provides a means of recovering the chymosin and separating it from contaminants other than pepsin.

The present invention is further directed in part to the unexpected discovery that when the polyethylene glycol phase is then contacted with an ion exchange resin under conditions wherein the chymosin binds to the resin, the polyethylene glycol and pepsin will pass through the resin. Accordingly, when these two steps are combined, the method of the present invention permits the recover y and purification of chymosin which is substantially free of pepsin and other contaminants.

However, prior to discussing this invention in detail, the following terms will first be defined:

"Naturally produced chymosin"—refers to chymosin obtained from mammalian sources including, for example, the stomachs of bovine (including the fourth stomachs of calves), of goat, of porcine, of lamb, etc.

"Pepsin"—refer to pepsin obtained from mammalian sources including, for example, the stomachs of bovine (including the fourth stomach of calves), of goat, or porcine, of lamb, etc. In addition to chymosin, pepsin is also recovered in the extraction of macerated stomachs.

"Other contaminants"—refer to components, other than chymosin and pepsin, obtained during the extraction of mammalian macerated stomachs. Such other contaminants include, for example, proteins (e.g., albumin), enzymes and the like.

"Aqueous solutions containing naturally produced chymosin, pepsin and other contaminants"—refers to aqueous solutions obtained by extracting macerated mammalian stomach tissue so as to obtain naturally produced chymosin. Methods for preparing (macerating) and extracting chymosin from such tissue are well known in the art and are described, for example, in "Fundamentals of Dairy Chemistry", 2nd Ed., Webb et al. Editors, AVI Publishing Company, pp. 674-679, (1983). Such known extraction procedures also extract pepsin from the stomach tissue as well as other contaminants. In general, the amount of pepsin extracted into the aqueous solution depends on factors such as the age of the animal from which the stomach was obtained as well as the whether the animal had been weaned. The stomach of a young animal which is still nursing will contain significantly more chymosin and less pepsin as compared to an older animal which had been weaned. On the other hand, the stomachs of such older animals still contain recoverable amounts of chymosin.

"Polyethylene glycol"—refers to any molecular weight polyethylene glycol which can be used to extract chymosin in the manner of this invention. Polyethylene glycol is available in molecular weights ranging from about 400 to about 22,000. Preferred polyethylene glycol for use herein should have a molecular weight in the range from about 600 to about 12,000. A particularly preferred polyethylene glycol is PEG-8000, i.e., polyethylene glycol having a molecular weight in the range of about 8,000. The selection of the polyethylene glycol used will depend in part on the composition of the mixture from which the chymosin is to be extracted and in part on economics of the process, as well as other factors.

"Inorganic salt"—refers to any inorganic salt which can be used to extract chymosin in the manner of this invention. Suitable inorganic salts include for instance, sulfate salts, phosphate salts, and the like. The sulfate salts are preferred including sodium sulfate, magnesium sulfate, ammonium sulfate, and the like. Additionally, mixtures of suitable salts can also be used as well as mixtures of such salts in combination with salt(s) such as sodium chloride, which by itself does not partition into a two phase system with polyethylene glycol but in combination with a suitable inorganic salt are known to enhance the partition coefficients of enzymes.

"Partition coefficient (K)"—is defined by the formula $$K = C_t/C_b$$

where $C_t$ refers to the equilibrium concentration of the partitioned compound in the top phase and $C_b$ refers to the equilibrium concentration of the partitioned compound in the bottom phase. Accordingly, it is apparent that the quantitative amount of partitioned compound in either phase depends on its partition coefficient as well as the volume of the phases. That is to say that if the partitioned compound has a partition coefficient of unity (the compound is equally partitioned in the top and bottom phases), then the phases will contain equal quantities of the partitioned compound only if the phases are of equal volume. If the top phase has 10% of the volume of the bottom phase, then when the partition coefficient is unity, the top phase will contain only 10% of the partitioned compound. In view of the above, it is further apparent that a very high partition coefficient for the partitioned compound is extremely valuable because it allows recovery of large quantities of this compound in the upper phase even when the volume of the upper phase is relatively small as compared to the bottom phase. Thus, in the present invention, very high partition coefficients allow for the use of smaller quantities of polyethylene glycol while still achieving very high recoveries of chymosin.

"Isoelectric point (IP)"—refers to the pH at which a polypeptide will be electrostatically neutral, i.e., the polypeptide carries an equal number of positive and negative charged functionalities. The isoelectric point for chymosin is about 4.6 and that for pepsin is also about 4.6. At a pH below the isoelectric point, chymosin and pepsin will have a net positive charge; and at a pH above the isoelectric point, chymosin and pepsin will have a net negative charge.

"Ion exchange resin"—refers to a protein compatible resinous material which is capable of electrostatically binding charged compounds. Ion exchange resins are well known in the art and include both cation and anion exchange resins.

In the practice of this invention, an aqueous polyethylene glycol solution containing chymosin and pepsin is contacted with an ion exchange resin under conditions wherein the chymosin will bind to the resin. Whether a cation or an anion exchange resin is employed in the present invention depends on the pH of the polyethylene glycol phase, i.e., whether the pH of the solution is above or below the isoelectric point of chymosin. Accordingly, contacting a solution containing chymosin with an ion exchange resin under conditions wherein the chymosin binds to the resin merely refers to adjusting the pH of the solution above or below its isoelectric point so that the chymosin binds to the resin employed.

On the other hand, it has unexpectedly been found that under these conditions, pepsin does not bind to the ion exchange resin even though pepsin has an isoelectric point similar to that of chymosin.

The pH of the aqueous polyethylene glycol solution is generally about 6.5 or less, although pH's around chymosin's isoelectric point, i.e., pH from about 3.6 to about 5.0, are not preferred due to the low net electrostatic charge of chymosin which reduces its effectiveness in binding to the resin. Additionally, when the polyethylene glycol solution (phase) is maintained at a pH between about 3-5, chymosin undergoes more efficient autolysis, although at a rate appreciably slower than in water. In any event, maintaining the aqueous polyethylene glycol phase at a pH between about 3-5 will result in some loss in chymosin yield due to autolysis. Accordingly, when a cation exchange resin is employed, it is preferred that the pH of the solution be maintained below about 3.0; whereas when an anion exchange resin is employed, it is preferred that the pH be maintained at above about 5.0.

Preferred cation exchange resins for use in this invention include, for instance, IBF SP-Spherodex, Pharmacia SP-Sephadex, Indion SP-2, IBF SP-Trisacryl, and the like. Preferred anion exchange resins for use in this invention include, for instance, IBF Q-Spherodex, Pharmacia Q-Sephadex, Indion Q-2, IBF Q-Trisacryl, and the like.

The processes of this invention are useful for recovery and purification of naturally produced chymosin.

When recovering and purifying naturally produced chymosin, the aqueous solution containing chymosin, pepsin and other contaminants may be used in its crude form, i.e., the solution obtained from extracting macerated stomach, or, if desired, the aqueous solution can first be filtered to remove most or all of the solids then the liquid filtrate used in the processes of this invention.

In the first step of this invention, naturally produced chymosin is recovered by adding to the aqueous solution containing chymosin, pepsin and other impurities, an effective amount of polyethylene glycol (PEG) and an effective amount of an inorganic salt so as to form a two phase system. The resulting solution is allowed to stand so as to separate into a chymosin and pepsin-rich polyethylene glycol phase and a chymosin and pepsin-poor salt phase. The chymosin and pepsin-rich polyethylene glycol phase is then recovered by conventional techniques.

It has been found that under these conditions, partition coefficients for chymosin and pepsin in the polyethylene glycol phase of greater than 30 and preferably greater than 85 are achieved. While polyethylene glycol extraction is useful for recovering chymosin at higher pH levels, i.e., pH 6.5 or less, it is more efficient when the process is conducted at a pH less than about 3. At such lower pHs, partition coefficients for chymosin/pepsin of up to 100 or more can be achieved. High partition coefficients are particularly advantageous because such permit the use of smaller quantities of polyethylene glycol to achieve the desired separation of chymosin from the fermentation beer which, in turn, facilitates the later separation of chymosin from the polyethylene glycol, i.e., there is less polyethylene glycol to separate.

It has further been found that as a result of a single extraction, the polyethylene glycol phase can contain as much as 95% or more of the total chymosin initially present in the aqueous solution and contains very little, if any, of contaminants other than pepsin. Thus, in addition to providing a means for recovering substantially all of the naturally produced chymosin and pepsin contained in the aqueous solution, this aspect of the present invention also provides a means of recovering the chymosin and separating it from contaminants other than pepsin.

In the next step of this invention, the polyethylene glycol phase containing the extracted chymosin and pepsin is separated from the other phase or phases and the polyethylene glycol phase is contacted with an ion exchange resin while maintaining or adjusting the pH so that the chymosin will bind to the resin. Because the polyethylene glycol is not charged, under these conditions, it passes through the resin. Surprisingly, under these conditions, the pepsin also does not bind to the ion exchange resin and passes through the resin. Thus, this step effects purification of chymosin not only from the polyethylene glycol but also from the pepsin. Thus, when the isolated polyethylene glycol phase containing the extracted chymosin and pepsin is contacted with the ion exchange resin under conditions where the chymosin binds to the resin, essentially all the chymosin comes out of the polyethylene glycol and is bound to the ion exchange resin and the polyethylene glycol and pepsin pass through the resin column. After the initial contact, the resin is washed with either water or water and salt, preferably under conditions that will not remove the chymosin from the resin, to remove the remaining polyethylene glycol and pepsin. Then the chymosin is eluted from the column using a salt solution and a buffer maintained at a pH which will remove the chymosin from the resin. Because of the high selectivity for chymosin recovery, it is unnecessary to use a gradient or step-wise elution of the resin because essentially the only enzyme or material which is bound by the resin from the polyethylene glycol phase and subsequently released from the resin is chymosin. Therefore, the chymosin can be eluted in one bulk step using the salt solution and raising or lowering the pH (depending of course, on whether a cation or anion exchange resin is employed) to cause the entire chymosin content bound to the resin to be eluted in one batch. Preferably, a salt is added to the eluting solution to aid in the rate or degree of elution, or in some cases, i.e., with an anion exchange resin, to effect elution of the chymosin from the resin, e.g. 50 mM sodium phosphate/2M NaCl, pH 5.8. Salts are preferably employed with the eluting solution since chymosin is usually sold in commercial form in a salt solution and accordingly, it is convenient to incorporate the salt with the chymosin at this point.

Thus, recovery and purification of chymosin in the manner of this invention will result in chymosin substantially free of pepsin and other contaminants, i.e., the amount of contamination is less than about 10% by weight based on the weight of chymosin and preferably, less than about 5% by weight based on the weight of the chymosin. That is to say that the resulting chymosin product is at least about 90% by weight pure and can be prepared for commercial use without further significant treatment to remove impurities. The commercial chymosin product is usually diluted to about 5 grams per gallon or about 1.5 grams per liter chymosin. The salt (usually NaCl) concentration is normally brought up to about 18% and a preservative such as sodium benzoate is added. The final concentration product intended for food grade use usually is also subjected to a final filtration to remove any undesirable solids or particles that may be present.

Although higher pH levels can be used throughout the process (pHs up to about 6.5), the efficiency of the polyethylene glycol/inorganic salt mixture in extracting the chymosin from the aqueous solution containing chymosin, pepsin and other contaminants and therefore the efficiency of the process is not as high as when low pH is maintained throughout the extraction step. Therefore, it is preferred to use low pH and accordingly, a cation exchange resin to increase the efficiency of the overall process.

When the preferred aspects of the above invention are combined by conducting the polyethylene glycol extraction at a pH of about 3 or below and contacting the separated polyethylene glycol phase with a cation exchange resin while maintaining the low pH, it has been found that a single polyethylene glycol extraction and a single-pass contact with the ion exchange resin will recover as much as 90 to 95% of the total chymosin present in the initial aqueous solution.

On the other hand, the use of a higher pH in the polyethylene glycol extraction step as well as an anion exchange resin while maintaining the pH above chymosin's isoelectric point also provides acceptable results. However, if a higher pH is employed to extract the chymosin and a lower pH is desired to contact the solution with resin, this can be readily achieved simply by adjusting the pH of the polyethylene glycol extract to below chymosin's isoelectric point and preferably, to about pH 3.6 or below and more preferably about pH 3 or below, and then contacting the chymosin with a cation exchange resin.

In addition to the high efficiency for chymosin and pepsin, especially chymosin, recovery by using the polyethylene glycol/inorganic salt mixture herein described, it has been further found that the solubility of chymosin in polyethylene glycol is apparently so high that the chymosin moves from the aqueous phase into the polyethylene glycol phase very rapidly. The time required for extraction of the chymosin into the polyethylene glycol phase is usually so short that it is not a significant process design factor. This process is therefore very efficient and economic in operation and is easily scaled up for commercial production.

As is apparent and regardless of the pH employed, the herein described process involves moving the chymosin and pepsin from the aqueous mixture into the more hydrophobic polyethylene glycol phase. This is driven, at least in part, by the salt concentration in the non-polyethylene glycol phase or phases. If a low molecular weight polyethylene glycol is used, the polyethylene glycol phase is less hydrophobic and a higher salt concentration is necessary in the non-polyethylene glycol phase(s), which adds to the cost of operation. If a higher molecular weight more hydrophobic polyethylene glycol is used, less salt will be needed in the process, but the separation rate may be lower because of the high viscosity of the higher molecular weight polyethylene glycol. Thus, the process of this invention can be optimized for any particular operation by selecting the desired polyethylene glycol molecular weight, the salt concentration and other parameters which provide the desired economics. One objective is usually to minimize the time required to move the chymosin into the polyethylene glycol phase, but another objective is usually to minimize the amount of salt used to effect the transfer of essentially all of the chymosin into the polyethylene glycol phase. While the salt concentration in the non-polyethylene glycol phases can be 20% by weight or higher, usually less than about 15% is required with the appropriate polyethylene glycol. For example, with PEG-8000, about 10-13% sodium sulfate is adequate. On the other hand, the minimum inorganic salt concentration is dictated by the concentration of the salt necessary to form a two phase system with polyethylene glycol. However, in a preferred embodiment, the inorganic salt concentration is from about 8.5 to about 20 weight to volume percent based on the volume of the aqueous solution containing chymosin, pepsin and other contaminants.

Also, preferably, the polyethylene glycol concentration employed herein is less than about 20, and more preferably less than about 15, weight to volume percent based on the volume of the aqueous solution containing chymosin, pepsin and other contaminants. For economics and ease of later separation, as little polyethylene glycol as possible is most preferably employed.

The exact concentration of polyethylene glycol and inorganic salt employed herein can readily be determined by the skilled artisan.

After the chymosin is bound by the ion exchange resin, the recovered polyethylene glycol phase is contaminated with pepsin. The pepsin can be recovered from this solution by known methods and the polyethylene glycol recycled. Alternatively, the polyethylene glycol can be discarded.

On the other hand, the ion exchange resin can be regenerated for use with subsequent batches of polyethylene glycol containing chymosin by washing the ion exchange resin with a solution of water adjusted to the appropriate pH. For example, when a cation exchange resin is employed, it can be regenerated by washing it with a solution of water containing enough sulfuric acid to make the pH about 2.

The above aspects of this invention which enable the reuse of the ion exchange resins particularly lend the processes of this invention to efficient commercial and industrial operation for the purification of industrial quantities of chymosin, particularly naturally produced chymosin.

Having described the invention in general terms the invention can be better understood by reference to the following embodiments of the invention which are illustrated in the following examples. However the scope of this invention is to be determined by the appended claims, whereas the following examples are merely illustrative embodiments of particular ways in which the invention disclosed herein can be practiced.

EXAMPLES

Example 1

This example describes the use of and aqueous two phase polyethylene glycol extraction process followed by contact with an ion exchange resin to produce food grade chymosin from bovine stomachs. The chymosin is recovered from beef (bovine) stomachs which contain large amounts of bovine pepsin and a lesser amount of chymosin. The aqueous solution employed herein is prepared by grinding bovine stomachs in a suitable liquid medium and filtering out the cell debris. The resulting aqueous solution contains naturally produced chymosin, pepsin and other contaminants.

In this example, 500 ml of beef extract was adjusted to pH 2 with sulfuric acid. 20 grams of PEG 8000 (4 wt. to vol. percent) and 55 grams of anhydrous sodium sulfate 11 wt. to vol. percent) were added to the extract. The extract was warmed to 37° C. to facilitate the solubility of the sulfate salt. The mixture was separated into two phases by centrifugation (Sorvall centrifuge) at about $5000 \times g$ for about 15 minutes and the polyethylene glycol phase (top phase) was separated from the salt phase (bottom phase) by removing the bottom phase with a perstaltic pump. The polyethylene glycol phase was diluted 1:3 with deionized water. The pH of this phase was determined to be 2.7 and was adjusted to 2.3 with sulfuric acid. The polyethylene glycol diluted phase was then passed over an ion exchange resin consisting of IBF Spherodex SP (a protein compatible cation exchange resin) which was previously equilibrated in water at pH 2 so as to bind the chymosin. The polyethylene glycol solution which flowed through was collected and was found to contain pepsin. The resin was eluted with a solution of 0.5M NaCl at pH 2.0 to remove any remaining polyethylene glycol and pepsin and the wash solution was collected. The resin was then eluted with a solution of 0.05M sodium phosphate at pH 5.8 containing 2M NaCl so as to release the chymosin in bulk. The eluted liquid containing chymosin substantially free of pepsin and other contaminants was then recovered.

For the purpose of distinguishing the relative amounts of bovine pepsin and chymosin in the product, the following assay was employed. The milk clotting ability of the various solutions was measured using a roller bottle apparatus. Skim milk was prepared at pH 6 and at 6.5. Bovine pepsin has more activity at pH 6 and chymosin has more activity at pH 6.5. The clotting activities are compared to a standard consisting of 90% chymosin, 10% pepsin. The ratio of activity at pH 6 to pH 6.5 is then a measure of the relative amounts of the two enzymes. The standard, by definition, provides a ratio of 1. Since bovine pepsin is more active at pH 6 than at pH 6.5, the ratio of activity at pH 6 and pH 6.5 will be greater than 1 and approach 2 for pure pepsin. On the other hand, for high levels of chymosin, the ratio will be less than 1 and approach 0.5 or less.

In this assay, the aqueous solution of chymosin, pepsin and other impurities had a total concentration of chymosin and pepsin of 16.64 CHU/ml (pH 6.5). After recovering the top phase, it was applied to the resin. The results of the resin wash are reported as flow through (the material which passed through the resin without binding); wash (the material which came of the resin during the washing step to remove pepsin and other contaminants); and the elute (the material recovered when the column was eluted so as to recover chymosin). The results of this assay are as follows:

| Sample assayed | Conc. of chymosin and pepsin | ratio (6/6.5) |
|---|---|---|
| starting material | — | 1.41 |
| extraction of 500 ml of starting material | 8320 CHU$^a$ (16.54 CHU/ml) | |
| top phase$^b$ | 7830 CHU (115.15 CHU/ml) | 1.34 |
| bottom phase | 454.5 CHU (1.01 CHU/ml) | — |
| flow through | 971.6 CHU (6.94 CHU/ml) | 1.08 |
| wash | 179.75 CHU (7.19 CHU/ml) | 1.54 |
| elute | 822.25 CHU (32.89 CHU/ml) | 0.49 |

$^a$CHU — Chris. Hansen Unit - 1 CHU/ml equals under the following conditions: Substrate: 110 g of low heat, spraydried skim milk powder is suspended in 1000 ml 0.05% calcium chloride. The milk is stirred for 30 minutes at room temperature and then left for rest for another 30 minutes. The milk should be stored at a temperature between 4 and 25° C. and not longer than 3 hours. The pH of the milk is about 6.5. Temperature: 32° C. plus or minus 0.2° C. in a thermostatic water bath.
Enzyme Addition: To 25 ml of the reconstituted skim milk is added 0.5 ml of enzyme solution, diluted to give a clotting time of between 380 and 500 seconds, and which will give a clotting time of 410 to 460 seconds.
$^b$the partition coefficient for chymosin/pepsin is 114

From the above data, it is apparent that the material recovered in the elute is chymosin substantially free of pepsin and other contaminant. Thus, the process of this invention permits the efficient recovery of chymosin from natural chymosin sources.

Likewise, by following the procedures set forth above, chymosin can likewise be recovered and purified by extracting at a pH of from about 5 to 6.5 and using an anion exchange resin. Suitable anion exchange resins which could be substituted for the cation exchange resin in the above example include, for instance, IBF Q-Spherodex, Pharmacia Q-Sephadex, Indion Q-2, IBF Q-Trisacryl, and the like.

Example 2

In a manner similar to the extraction procedure set forth in Example 1 above but using a pH of about 5.8, the enzymes listed below were separately extracted from an aqueous solution into the polyethylene glycol phase of the liquid-liquid two phase system to provide the following results (pure enzyme used):

| Enzyme | Protein (mg/ml) | Activity CHU/ml | Partition Coefficient |
|---|---|---|---|
| calf chymosin | 1.7 | 28 | 87 |
| bovine pepsin | 1.9 | 31 | 31.5 |
| porcine pepsin | 2.3 | 29.7 | 1.45 |
| E. parasitica aspartic protease | 3.6 | 27 | 0.33 |
| M. miehei aspartic protease | 2.4 | 20.5 | 0.24 |

This experiment was repeated but at this time at pH 2-2.5 with the following results:

| Enzyme | Protein (mg/ml) | Activity CHU/ml | Partition Coefficient |
|---|---|---|---|
| calf chymosin | 1.2 | 89 | >943$^c$ |
| bovine pepsin | 1.3 | 50 | >462$^c$ |
| porcine pepsin | 1.6 | 23.7 | >206$^c$ |
| E. parasitica aspartic protease | 2.5 | 15.2 | 1.18 |
| M. miehei aspartic protease | 1.7 | 48 | 0.94 |

$^c$Partition coefficients of about 200 or more are difficult to measure accurately because of assay limitations. That is to say that because the partition coefficient is a ratio of the concentration of chymosin in the top phase divided by the concentration of the chymosin in the bottom phase and further because the amount of chymosin in the bottom phase is generally very small, small changes in this bottom concentration will produce large swings in the partition coefficient. Moreover, the concentration determined by assay methodology is particularly subject to variations at very low concentrations.

The above results indicate that chymosin and pepsin have high partition coefficients in this system. However, it is also clear that the partition coefficients for bovine pepsin increase substantially in going from pH 5.8 to pH 2-2.5. Accordingly, it may be preferable to conduct the extraction at a pH above about 5 so as to reduce the amount of pepsin in the polyethylene glycol phase. On the other hand, the partition coefficients for chymosin also increase substantially in going from pH 5.8 to pH 2-2.5. Thus, if the extraction is done at a pH above about 5, the amount of chymosin recovered would also be somewhat reduced, albeit at a lower level because chymosin's partition coefficient at pH 5.8 is higher than that of bovine pepsin.

What is claimed is:

1. A method for recovering and purifying chymosin from an aqueous solution which contains chymosin obtained from natural sources and which additionally contains pepsin and other contaminants which method comprises:
   a) adding to the aqueous solution an effective amount of polyethylene glycol (PEG) and an inorganic salt so as to form a two phase system;
   b) allowing the aqueous solution-polyethylene glycol-inorganic salt mixture to separate into a chymosin and pepsin-rich polyethylene glycol phase and a chymosin and pepsin-poor salt phase;
   c) recovering the chymosin and pepsin-rich polyethylene glycol phase,
   d) contacting the chymosin and pepsin-rich polyethylene glycol phase with an ion exchange resin under conditions wherein the chymosin binds to the resin and the polyethylene glycol and pepsin pass through the resin; and
   e) recovering the chymosin from the resin.

2. A method according to claim 1 wherein the pH of the aqueous solution is about 6.5 or less.

3. A method according to claim 2 wherein the pH of the aqueous solution is about 3 or less.

4. A method according to claim 3 wherein the pH of the aqueous solution is less than about 2.8.

5. A method according to claim 1 wherein the average molecular weight of the polyethylene glycol is from about 600 to about 12,000.

6. A method according to claim 5 wherein the average molecular weight of the polyethylene glycol is from about 5,000 to about 10,000.

7. A method according to claim 1 wherein said inorganic salt is selected from the group consisting of sulfate salts, and phosphate salts.

8. A method according to claim 7 wherein said inorganic salt is a sulfate salt.

9. A method according to claim 8 wherein said sulfate salt is selected from the group consisting of sodium sulfate, magnesium sulfate, and ammonium sulfate.

10. A method according to claim 1 wherein said aqueous solution is first filtered prior to addition of said polyethylene glycol and said inorganic salt.

11. A method according to claim 1 wherein the pH of said chymosin and pepsin-rich polyethylene glycol phase is either from 5.0 to 6.5 or is about 3.0 or less.

12. A method according to claim 11 wherein the pH of said chymosin and pepsin-rich polyethylene glycol phase is about 3.0 or less and a cation exchange resin is employed.

13. A method according to claim 12 wherein the pH of said chymosin and pepsin-rich polyethylene glycol phase is from about 2.0 to 2.5.

14. A method according to claim 11 wherein the pH of said chymosin and pepsin-rich polyethylene glycol phase is from about 5.0 to about 6.5 and an anion exchange resin is employed.

15. A method according to claim 1 wherein the extraction step a) is conducted at a pH of about 3.0 or less and after isolation of the polyethylene glycol phase, the pH of this phase is adjusted to from about 5.0 to about 6.5 and an anion exchange resin is employed.

16. A method for recovering and purifying chymosin from an aqueous solution which contains chymosin obtained from natural sources and which additionally contains pepsin and other contaminants which method comprises:
a) adjusting the pH of the aqueous solution to less than about 3 and then adding to the aqueous solution an effective amount of polyethylene glycol (PEG) and an inorganic salt so as to form a two phase system;
b) allowing the aqueous solution-polyethylene glycol-inorganic salt mixture to separate into a chymosin and pepsin-rich polyethylene glycol phase and a chymosin and pepsin-poor salt phase;
c) recovering the chymosin and pepsin-rich polyethylene glycol phase,
d) contacting the chymosin and pepsin-rich polyethylene glycol phase with a cation exchange resin under conditions wherein the chymosin binds to the resin and the polyethylene glycol and pepsin pass through the resin; and
e) recovering the chymosin from the resin.

17. A method according to claim 16 wherein the average molecular weight of the polyethylene glycol is from about 600 to about 12,000.

18. A method according to claim 17 wherein the average molecular weight of the polyethylene glycol is from about 5,000 to about 10,000.

19. A method according to claim 16 wherein said inorganic salt is selected from the group consisting of sulfate salts, and phosphate salts.

20. A method according to claim 19 wherein said inorganic salt is a sulfate salt.

21. A method according to claim 20 wherein said sulfate salt is selected from the group consisting of sodium sulfate, magnesium sulfate, and ammonium sulfate.

22. A method according to claim 16 wherein said aqueous solution beer is first filtered prior to addition of said polyethylene glycol and said inorganic salt.

23. A method for recovering and purifying chymosin from an aqueous solution which contains chymosin obtained from bovine sources and which additionally contains pepsin and other contaminants which method comprises:
a) maintaining the pH of the aqueous solution at about 6.5 or less;
b) adding to the aqueous solution an effective amount of polyethylene glycol (PEG) having an average molecular weight of from about 600 to about 12,000 and an effective amount of an inorganic salt selected from sulfate and phosphate salts so as to form a two phase system;
c) allowing the aqueous solution-polyethylene glycol-inorganic salt mixture to separate into a chymosin and pepsin-rich polyethylene glycol phase and a chymosin and pepsin-poor salt phase;
d) recovering the chymosin and pepsin-rich polyethylene glycol phase;
e) contacting the chymosin and pepsin-rich polyethylene glycol phase with an ion exchange resin under conditions wherein the chymosin binds to the resin and the polyethylene glycol and pepsin pass through the resin; and
f) recovering the chymosin from the resin.

24. The method according to claim 23 wherein the bovine source is the fourth stomach of calves.

25. A method for recovering and purifying chymosin from an aqueous solution which contains chymosin obtained from bovine sources and which additionally contains pepsin and other contaminants which method comprises:
a) maintaining the pH of the aqueous solution at from about 5 to about 6.5;
b) adding to the aqueous solution an effective amount of polyethylene glycol (PEG) having an average molecular weight of from about 600 to about 12,000 and an effective amount of an inorganic salt selected from sulfate and phosphate salts so as to form a two phase system;
c) allowing the aqueous solution-polyethylene glycol-inorganic salt mixture to separate into a chymosin and pepsin-rich polyethylene glycol phase and a chymosin and pepsin-poor salt phase;
d) recovering the chymosin and pepsin-rich polyethylene glycol phase;
e) contacting the chymosin and pepsin-rich polyethylene glycol phase with an ion exchange resin under conditions wherein the chymosin binds to the resin and the polyethylene glycol and pepsin pass through the resin; and
f) recovering the chymosin from the resin.

26. The method according to claim 25 wherein the bovine source is the fourth stomach of calves.

27. A method for recovering and purifying chymosin from an aqueous solution which contains chymosin obtained from bovine sources and which additionally contains pepsin and other contaminants which method comprises:

a) maintaining the pH of the aqueous solution at about 3 or less;

b) adding to the aqueous solution an effective amount of polyethylene glycol (PEG) having an average molecular weight of from about 600 to about 12,000 and an effective amount of an inorganic salt selected from sulfate and phosphate salts so as to form a two phase system;

c) allowing the aqueous solution-polyethylene glycol-inorganic salt mixture to separate into a chymosin and pepsin-rich polyethylene glycol phase and a chymosin and pepsin-poor salt phase;

d) recovering the chymosin and pepsin-rich polyethylene glycol phase;

e) contacting the chymosin and pepsin-rich polyethylene glycol phase with an ion exchange resin under conditions wherein the chymosin binds to the resin and the polyethylene glycol and pepsin pass through the resin; and f) recovering the chymosin from the resin.

28. The method according to claim 27 wherein the bovine source is the fourth stomach of calves.

* * * * *

UNITED STATES PATENT AND TRADEMARK OFFICE
CERTIFICATE OF CORRECTION

PATENT NO. : 5,151,358
DATED : September 29, 1992
INVENTOR(S) : Henry G. Heinsohn, et al.

It is certified that error appears in the above-identified patent and that said Letters Patent is hereby corrected as shown below:

Column 2, line 56, delete "eliminate" and insert in place thereof --eliminated--.

Column 3, line 39, delete "peps in-rich" and insert in place thereof --pepsin-rich--.

Column 4, line 56, delete "recover y" and insert in place thereof --recovery--; and line 66, delete "or" and insert in place thereof --of--.

Column 5, line 20, delete "the whether" and insert in place thereof --whether--.

Column 7, line 39, delete "of".

Column 10, line 25, delete "and" and insert in place thereof --an--.

UNITED STATES PATENT AND TRADEMARK OFFICE
CERTIFICATE OF CORRECTION

PATENT NO. : 5,151,358

DATED : September 29, 1992

INVENTOR(S) : Henry G. Heinsohn, et al.

It is certified that error appears in the above-identified patent and that said Letters Patent is hereby corrected as shown below:

Column 11, line 18, delete "of" and insert in place thereof --off--; line 37, delete "left for" and insert in place thereof --left to--; and line 44, delete "contaminant" and insert in place thereof --contaminants--.

Column 12, line 56, delete "," and insert in place thereof --;--.

Column 13, line 53, delete "," and insert in place thereof --;--.

Column 14, line 57, delete "ion" and insert in place thereof --anion--.

Column 16, line 6, delete "an ion" and insert in place thereof --a cation--.

Signed and Sealed this

Twenty-fifth Day of January, 1994

Attest:

BRUCE LEHMAN

Attesting Officer

Commissioner of Patents and Trademarks